US00PP10193P

United States Patent [19]

Elliot et al.

[11] Patent Number: Plant 10,193

[45] Date of Patent: Jan. 13, 1998

[54] *BRACTEANTHA BRACTEATA* PLANT NAMED 'GOLD 'N' BRONZE'

[75] Inventors: Winston Rodger Elliot; Gwendoline Margaret Elliot, both of Heathmont, Australia

[73] Assignee: Koala Blooms Pty. Ltd., Mordiallov, Australia

[21] Appl. No.: 694,150

[22] Filed: Aug. 8, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 9,660 10/1996 Bautista ..... Plt./68.1
P.P. 9,661 10/1996 Bautista ..... Plt./68.1
P.P. 9,666 10/1996 Bautista ..... Plt./68.1
P.P. 9,667 10/1996 Bautista ..... Plt./68.1

OTHER PUBLICATIONS

UPOV Rom Jan. 1997 Data Printout, 1997.

*Primary Examiner*—James R. Feyrer
*Assistant Examiner*—Kent L. Bell
*Attorney, Agent, or Firm*—C. A. Whealy

[57] ABSTRACT

A new and distinct cultivar of *Bracteantha bracteata* named 'Gold 'N' Bronze', characterized by its rounded plant form; fast crop time; freely branching plant habit; narrow leaves; numerous medium-sized inflorescences; ray florets that are initially golden yellow and become bronze orange with development giving a gold and bronze bicolor appearance to the inflorescence; numerous ray florets; and long, erect peduncles that hold inflorescences above the foliage.

1 Drawing Sheet

The present invention relates to a new and distinct cultivar of Helichrysum plant, botanically known as *Bracteantha bracteata* and named 'Gold 'N' Bronze'. It is anticipated that the plant of this application will be marketed under the name "Nullarbor Gold 'N' Bronze".

The new cultivar originated from a cross made by the inventors of the *Bracteantha bracteata* cultivar 'Diamond Head' (not patented), as the male or pollen parent, with the *Bracteantha bracteata* cultivar 'Golden Bowerbird' (not patented), as the female or seed parent. The cultivar 'Gold 'N' Bronze' was discovered and selected by the inventors as a flowering plant within the progeny of the stated cross in a controlled environment in Montrose, Victoria, Australia in 1990.

Asexual reproduction of the new cultivar by terminal cuttings taken in a polyethylene-covered greenhouse in Montrose, Victoria, Australia, has shown that the unique features of this new Helichrysum are stable and are reproduced true to type in successive propagations.

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Gold 'N' Bronze', which in combination distinguish this Helichrysum from other Helichrysums, specifically the cultivars 'Diamond Head' and 'Golden Bowerbird', and distinguish 'Gold 'N' Bronze' as a new and distinct cultivar:

1. Rounded plant form. Plants of the cultivar 'Diamond Head' have a flat plant form and are shorter than plants of the new Helichrysum.

2. Fast crop time. Plants of the cultivar 'Diamond Head' flower later than plants of the new Helichrysum.

3. Freely branching. Plants of the cultivar 'Diamond Head' are not as freely branching as plants of the new Helichrysum.

4. Narrow leaves. Plants of the cultivars 'Diamond Head' and 'Golden Bowerbird' have broader leaves than plants of the new Helichrysum.

5. Numerous inflorescences. Plants of the cultivar 'Diamond Head' have fewer inflorescences than plants of the new Helichrysum.

6. Medium-sized inflorescences. Plants of the cultivar 'Diamond Head' have smaller inflorescences and plants of the cultivar 'Golden Bowerbird' have larger inflorescences than plants of the new Helichrysum.

7. Ray florets that are initially golden yellow and become bronze orange with development giving a gold and bronze bicolor appearance to the inflorescence. Plants of the cultivar 'Diamond Head' have golden yellow ray florets that do not become bronze with development.

8. Numerous ray florets. Plants of the cultivar 'Diamond Head' have fewer whorls of ray florets than plants of the new Helichrysum.

9. Long, erect peduncles that hold inflorescences above the foliage. Plants of the cultivar 'Diamond Head' have shorter peduncles than plants of the new Helichrysum.

A detailed comparison of the differences between the cultivars 'Gold 'N' Bronze' and 'Diamond Head' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a single potted plant of 'Gold 'N' Bronze'.

The second photograph comprises a top perspective view of developing inflorescences of plants of 'Gold 'N' Bronze'. Flower color in the photographs may appear different from the actual flower color due to light reflectance.

The following observations, measurements, values, and comparisons describe plants grown in Montrose, Victoria, Australia, under outdoor conditions with day temperatures ranging from 15° to 30° C. and night temperatures ranging from 5° to 18° C. and light levels from 5,000 to 9,000 footcandles. Color references are made to The Royal Horticultural Society Colour Chart except where general terms of ordinary dictionary significance are used.

lassification:

*Botanical.*—*Bracteantha bracteata* cultivar 'Gold 'N' Bronze'.

*Commercial.*—Helichrysum.

arentage:

*Male or pollen parent.*—*Bracteantha bracteata* cultivar 'Diamond Head'.

*Female or seed parent.*—*Bracteantha bracteata* cultivar 'Golden Bowerbird'.

:opagation:

*Type.*—*By cuttings.*

*Time to initiate and develop roots.*—*Summer:* 20 to 35 days at temperatures of 25° C. Winter: 25 to 50 days at temperatures of 20° C.

*Rooting habit.*—Fibrous and freely branching.

ant description:

*General appearance.*—Rounded spreading herbaceous plant with narrowly lanceolate foliage and erect flower stems. Appropriate for 12.5 pots to 25-cm hanging basket containers. To produce a finished plant from rooted cuttings, 12 to 16 weeks are required depending on temperature and light level.

*Plant height.*—About 22 cm from soil level to top of inflorescences.

*Branching.*—Moderate, 3 to 8 lateral branches develop when the terminal apex is removed (pinched). Lateral branches are typically 8 to 15 cm in length.

*Growth rate.*—Moderate.

*Vigor.*—Moderate.

*Foliage description.*—Arrangement: Alternate, single. Angle: Horizontal to upright. Quantity: 20 to 40 per lateral branch. Leaf shape: Narrowly lanceolate. Leaf margin: Entire. Leaf apex: Acute. Leaf base: Tapered. Leaf aspect: Flat. Leaf length: About 6.8 cm. Leaf width: About 4.7 mm. Leaf texture: Slightly rough, pubescent with minute hairs, prominent midribs. Leaf attachment: Sessile, slightly perfoliate. Leaf color: Young and fully expanded leaves: Abaxial surface: 137A. Adaxial surface: 137C.

owering description:

*Inflorescence.*—Daisy-type composite inflorescence form. Flowers arranged acropetally on a capitulum. Inflorescences last on the plant for 4 to 5 weeks, about 2 weeks as a fresh cut flower, and more than 6 months as a dried cut flower. Inflorescences persistent.

*Natural flowering season.*—Natural flowering season is spring to fall. Plants flower continuously during this period.

*Quantity of inflorescences.*—One to six per lateral branch.

*Inflorescence diameter.*—3.5 to 4.5 cm.

*Inflorescence depth (height).*—About 2.5 cm.

*Fragrance.*—Slight honey.

*Ray florets.*—Quantity: 11 to 14 whorls of florets per inflorescence. Appearance: Satiny. Texture: Papery. Shape: Broadly elliptic. Margin: Entire. Tip: Acute. Length: 1 to 1.5 cm. Width: 4 to 6 mm. Color: When opening, abaxial surface: 12A. Mature, abaxial surface: Initially golden yellow, 12A, becoming more bronze orange, 24A, with development. With further development, florets turn brown, 166D. Mature, adaxial surface: 166D.

*Disc florets.*—Shape: Tubular. Diameter of disc: 1 to 1.5 cm. Color: Immature: 17A. Mature: 24A. Number of disc florets per inflorescence: Numerous.

*Peduncle.*—Length: About 20 cm. Strength: Moderately strong, inflorescences held erect above foliage. Color: 144A. Texture: Slightly pubescent.

*Flower bud.*—Shape: Globular. Length: About 2 cm. Diameter: About 2.8 cm. Color: 166D.

*Androecium.*—Only present on disc florets. Stamen number: Five per disc floret. Anther shape: Cylindrical. Pollen color: 23A.

*Gynoecium.*—Present on both ray and disc florets. Pistil number: One per floret. Style: Length: About 7 min. Color: 23A. Stigma color: 23A.

Disease resistance:

No susceptibility nor resistance to fungal, bacterial or viral pathogens has been noted.

Seed production: Seed production is typically not observed.

CHART A

| CHARACTERISTIC | GOLD 'N' BRONZE' | 'DIAMOND HEAD' |
|---|---|---|
| PLANT SHAPE | Rounded | Flat |
| PLANT HEIGHT | About 22 cm | About 13.6 cm |
| CROP TIME | 12 to 16 weeks | 14 to 20 weeks |
| NUMBER OF LATERAL BRANCHES FROM PINCHING | 3 to 8 | 2 to 5 |
| LATERAL BRANCH LENGTH | 8 to 15 cm | 2 to 10 cm |
| QUANTITY OF LEAVES | 20 to 40 per lateral branch | 20 to 35 per lateral branch |
| LEAF COLOR, YOUNG LEAVES, ABAXIAL SURFACE | 137A | 147A |
| LEAF COLOR, YOUNG LEAVES, ADAXIAL SURFACE | 137C | 146B |
| LEAF COLOR, MATURE LEAVES, ABAXIAL SURFACE | 137A | 147A |
| LEAF COLOR, MATURE LEAVES, ADAXIAL SURFACE | 137C | 146C |
| LEAF SHAPE | Narrowly lanceolate | Lanceolate |
| LEAF LENGTH | About 6.8 cm | About 7.6 cm |
| LEAF WIDTH | About 4.7 cm | About 7.3 cm |
| QUANTITYOF INFLORESCENCES PER STEM | 1 to 6 | 1 to 3 |
| INFLORESCENCE DIAMETER | 3.5 to 4.5 cm | 2.5 to 3.5 cm |
| INFLORESCENCE DEPTH | About 2.5 cm | About 1.5 cm |
| RAY FLORET SHAPE | Broadly elliptic | Lanceolate to broadly elliptic |
| RAY FLORET LENGTH | 1 to 1.5 cm | 1.2 to 1.8 cm |
| RAY FLORET WIDTH | 4 to 6 mm | 3 to 6 mm |
| RAY FLORET COLOR, WHEN OPENING | 12A | 14B |
| RAY FLORET COLOR, MATURE ABAXIAL SURFACE | Initially 12A becoming orange, 24A, with further development | 14B |
| RAY FLORET COLOR, MATURE ADAXIAL SURFACE | 166D | 20A |
| NUMBER OF WHORLS OF RAY FLORETS PER INFLORESCENCE | About 12.6 | About 5.6 |
| DISC FLORET COLOR, IMMATURE | 17A | 24A |
| DISC FLORET COLOR, MATURE | 24A | 26A |
| PEDUNCLE LENGTH | About 20 cm | About 14 cm |

It is claimed:

1. A new and distinct cultivar of *Bracteantha bracteata* plant named 'Gold 'N' Bronze', as illustrated and described.

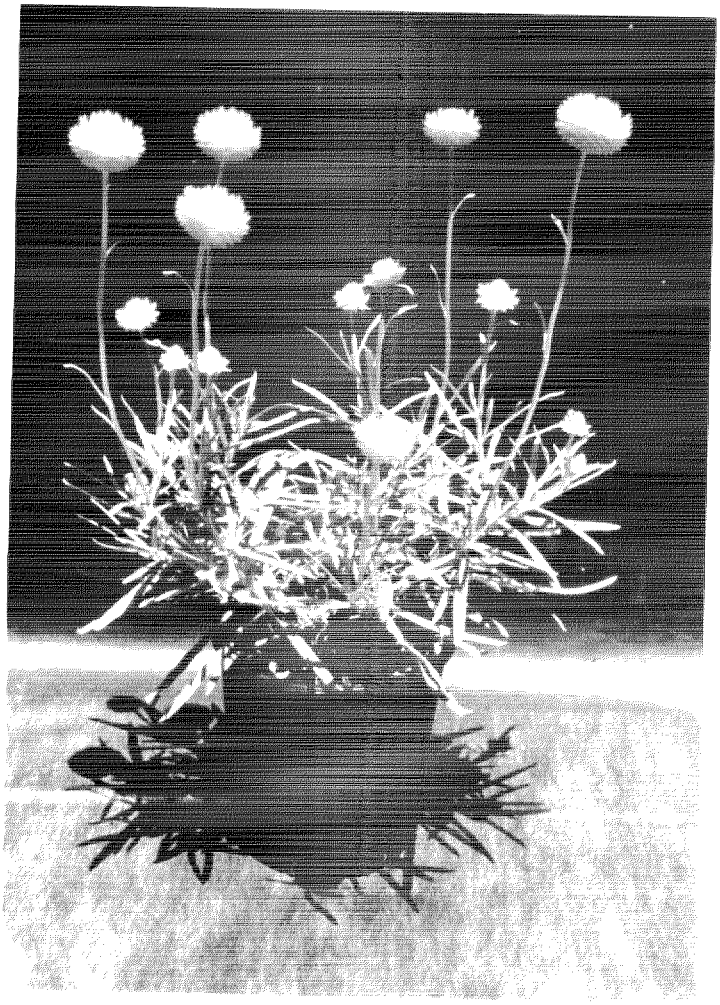
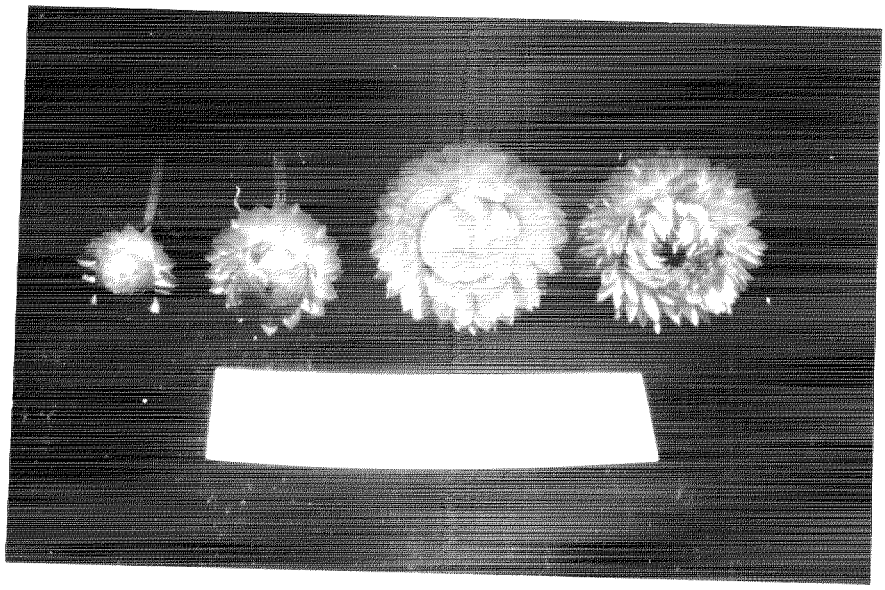

* * * * *